United States Patent
Gentile

(10) Patent No.: US 10,442,583 B2
(45) Date of Patent: Oct. 15, 2019

(54) METHOD FOR MANUFACTURING A DISPENSING DEVICE FOR EYE DROPS

(71) Applicant: DOMPE' FARMACEUTICI S.P.A., Milan (IT)

(72) Inventor: Marco Maria Gentile, L'Aquila (IT)

(73) Assignee: DOMPE' FARMACEUTICI S.P.A., Milan (IT)

( * ) Notice: Subject to any disclaimer, the term of this patent is extended or adjusted under 35 U.S.C. 154(b) by 90 days.

(21) Appl. No.: 15/564,286

(22) PCT Filed: Apr. 7, 2016

(86) PCT No.: PCT/IB2016/051965
§ 371 (c)(1),
(2) Date: Oct. 4, 2017

(87) PCT Pub. No.: WO2016/162814
PCT Pub. Date: Oct. 13, 2016

(65) Prior Publication Data
US 2018/0134468 A1 May 17, 2018

(30) Foreign Application Priority Data
Apr. 10, 2015 (IT) .............................. MI2015A0513

(51) Int. Cl.
*B65D 47/18* (2006.01)
*B65B 3/04* (2006.01)
(Continued)

(52) U.S. Cl.
CPC ............ *B65D 47/18* (2013.01); *A61F 9/0008* (2013.01); *B21D 53/00* (2013.01); *B65B 3/04* (2013.01);
(Continued)

(58) Field of Classification Search
CPC ................ B65D 81/3211; B65D 47/18; B65D 81/3227; B65D 81/3216; Y10T 29/53343;
(Continued)

(56) References Cited

U.S. PATENT DOCUMENTS 3,857,423 A 12/1974 Ronca
4,153,057 A 5/1979 Kobel
(Continued)

FOREIGN PATENT DOCUMENTS

CN 1229395 A 9/1999
EP 0459182 A2 12/1991
(Continued)

OTHER PUBLICATIONS

PCT International Search Report and Written Opinion dated Jul. 11, 2016 for Intl. App. No. PCT/IB2016/051965, from which the instant application is based, 8 pgs.
(Continued)

*Primary Examiner* — Jermie E Cozart
(74) *Attorney, Agent, or Firm* — Fredrikson & Byron, P.A.

(57) ABSTRACT

A process for the production of a device for dispensing eye drops. The process includes the steps of providing a first container and a second container configured to be engaged in a fluid-tight manner, providing a spacer, introducing a water-based solution inside the first container, introducing a solution or dispersion comprising a drug inside the second container, arranging the spacer between the first and second containers, engaging in a fluid-tight manner the second container and the first container, and freeze-drying the solution or dispersion comprising the drug.

14 Claims, 2 Drawing Sheets

(51) Int. Cl.
*B21D 53/00* (2006.01)
*A61F 9/00* (2006.01)
*B65D 81/32* (2006.01)
*F26B 5/06* (2006.01)
*F26B 25/06* (2006.01)

(52) U.S. Cl.
CPC .......... *B65D 81/3211* (2013.01); *F26B 5/065* (2013.01); *F26B 25/063* (2013.01); *B65D 81/3216* (2013.01); *B65D 81/3227* (2013.01); *Y10T 29/53343* (2015.01)

(58) Field of Classification Search
CPC ... B65B 3/04; B21D 53/00; F26B 5/06; F26B 5/065
See application file for complete search history.

(56) References Cited

U.S. PATENT DOCUMENTS

| | | | | |
|---|---|---|---|---|
| 5,685,845 A | * | 11/1997 | Grimard | A61J 1/2096 604/416 |
| 5,692,644 A | * | 12/1997 | Gueret | B05B 11/0083 206/222 |
| 5,964,043 A | * | 10/1999 | Oughton | F26B 5/06 34/284 |
| 2006/0049127 A1 | * | 3/2006 | Katz | B65D 81/3211 215/6 |
| 2007/0181449 A1 | | 8/2007 | Hamamoto et al. | |
| 2008/0108045 A1 | | 5/2008 | Ghinelli | |
| 2008/0314775 A1 | | 12/2008 | Owoc | |
| 2014/0008366 A1 | | 1/2014 | Genosar | |

FOREIGN PATENT DOCUMENTS

| | | |
|---|---|---|
| EP | 1009356 A1 | 6/2000 |
| FR | 2427960 A1 | 1/1980 |

OTHER PUBLICATIONS

PCT Demand materials, including amended claims, dated Feb. 7, 2017 for Intl. App. No. PCT/IB2016/051965, from which the instant application is based, 21 pgs.

International Preliminary Report on Patentability dated Mar. 28, 2017 for Intl. App. No. PCT/IB2016/051965, from which the instant application is based, 6 pgs.

* cited by examiner

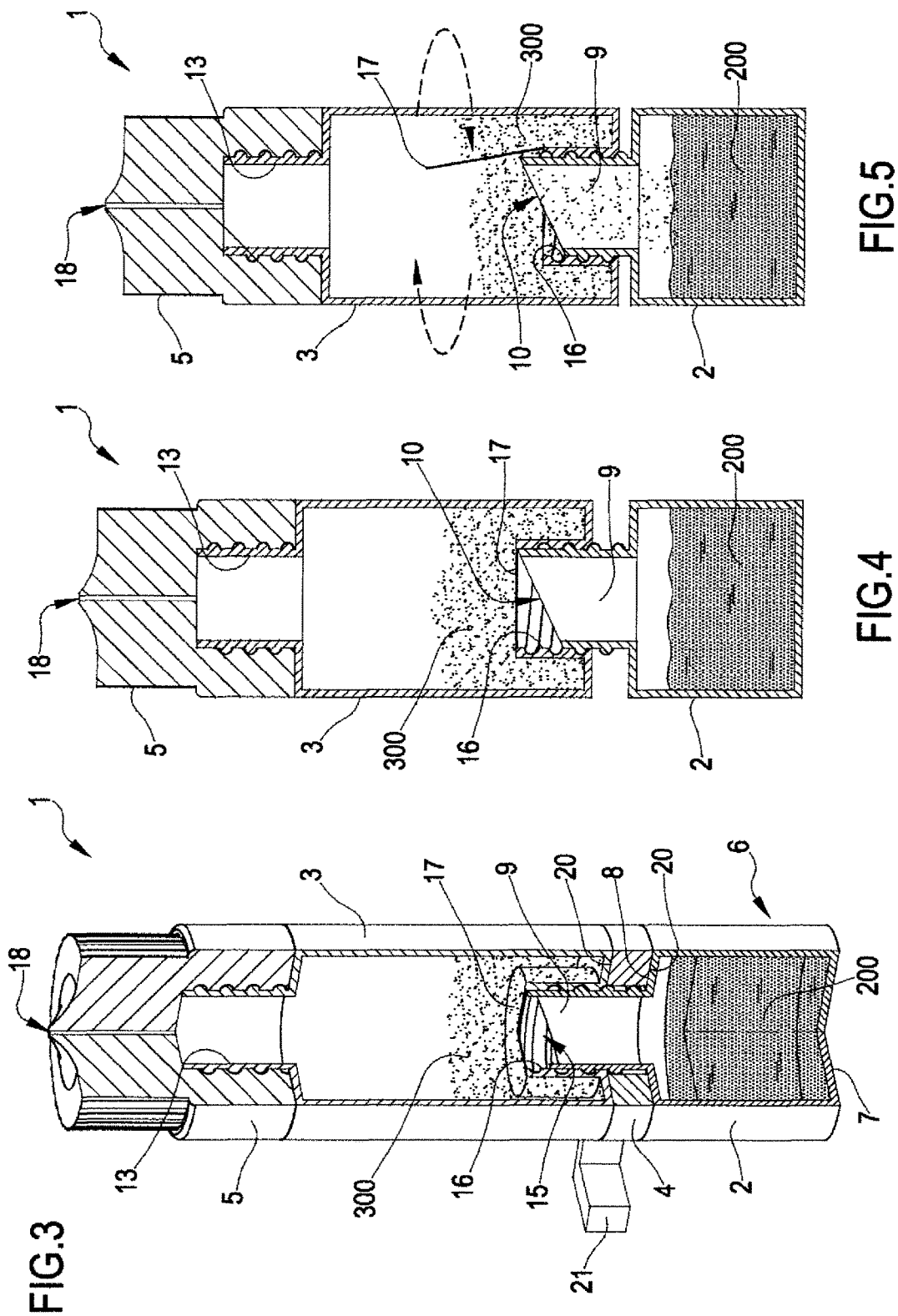

METHOD FOR MANUFACTURING A DISPENSING DEVICE FOR EYE DROPS

RELATED APPLICATIONS

This application is a 35 U.S.C. 371 national stage filing from International Application No. PCT/IB2016/051965, filed Apr. 7, 2016, which claims priority to Italian Application No. MI2015A000513, filed Apr. 10, 2015, the teachings of which are incorporated herein by reference.

FIELD OF THE INVENTION

The present invention relates to a device for dispensing eye drops, a process for the production of a device for dispensing eye drops and a process for preparing a multidose eye solution. In particular the present invention relates to a device for dispensing eye drops containing a first substance and at least one second substance comprising a therapeutic agent.

BACKGROUND

Drop dispensing devices are known. The known drop dispensing devices usually have a main body and a dropper engaged with the main body. The purpose of the dropper is to allow, upon administration, dosing of the substance contained inside it, so as to simplify the dispensing of a predetermined quantity of drops.

Also known are devices designed to contain two different substances inside respective containers. These containers may be configured to prevent mixing of the two substances or allow mixing thereof, for example in order to prepare a solution.

The devices described above have, however, a number of drawbacks. First of all, in the known devices keeping separate the two substances contained inside the respective containers is a complex operation; the known devices therefore are unable to ensure optimum separation of the two substances. This drawback is particularly disadvantageous since, should mixing of the substances occur at the wrong moment, it may result in incorrect preparation of the solution intended to be dispensed by the device.

BRIEF SUMMARY OF EMBODIMENTS OF THE INVENTION

In the light of the above, the main object of the present invention is to solve one or more of the problems encountered in the prior art.

One object of the present invention is to provide a drop dispensing device which is compact, simple and reliable.

Another object of the present invention is to provide a drop dispensing device which is able to simplify the formation of a solution intended to be dispensed by the device.

A further object of the present invention is to provide a process for the production of a drop dispensing device able to be automated in a simple and reliable manner. Furthermore an object of the present invention is to provide a process for preparing a multidose eye solution which is simple and rapid.

These objects along with others, which will become clearer from the following description, are essentially achieved by a drop dispensing device, a process for producing a drop dispensing device and a process for preparing a multidose eye solution in accordance with that stated in one or more of the attached claims and/or the following aspects, considered singly or in any combination with each other or in combination with any one of the attached claims and/or in combination with any one of the further aspects or characteristics described below.

According to a 1st aspect, a device (1) for dispensing eye drops is provided, said device comprising:
 a first container (2) containing a first substance,
 a second container (3) containing a second substance comprising a therapeutic agent.
the first container (2) comprising a tubular element (9) having an end portion (10) open so as to allow the first substance to flow through said open end portion (10), the second container (3) comprising a wall (16) configured to be engaged in a fluid-tight manner around the tubular element (9).

According to a 2nd aspect in accordance with the 1st aspect, the first and second substances are in a state of aggregation different from each other.

According to a 3rd aspect in accordance with the 1st or 2nd aspect, the first substance is liquid and the second substance is freeze-dried.

According to a 4th aspect in accordance with the 1st or 2nd or 3rd aspect, the first substance is water or a water-based solution for injection (200) and the second substance is a freeze-dried composition (300) comprising a drug. The drug may be of a chemical and/or biotechnological nature, for example may comprise the nerve growth factor.

According to a 5th aspect in accordance with any of the 1st to 4th aspects, the second container (3) comprises a piercible barrier (17) intended to prevent mixing of the first substance with the second substance.

According to 6th aspect in accordance with the 5th aspect, the piercible barrier (17) is configured to operate between at least one closed condition, in which it prevents mixing of the first substance with the second substance, and an open condition, in which it allows mixing of the first substance with the second substance.

According to a 7th aspect in accordance with 6th aspect, the piercible barrier (17) is engaged with the second container (3) both in the closed condition and in the open condition.

According to an 8th aspect in accordance with the 5th or 6th or 7th aspect, the piercible barrier (17) is arranged in proximity to said wall (16) of the second container (3).

According to a 9th aspect in accordance with any one of 5th to 8th aspects, the piercible barrier (17) extends transversely with respect to said wall (16) of the second container (3).

According to a 10th aspect in accordance with any one of the 5th to 9th aspects, the tubular element (9) comprises means (11) for mechanically connecting together the first and second containers (2, 3) configured to engage in a fluid-tight manner with said wall (16) of the second container (3).

According to an 11th aspect in accordance with the 10th aspect, the end portion (10) of the tubular element (9) is configured to pierce the barrier (17).

According to a 12th aspect in accordance with the 10th or 11th aspect, the mechanical connection means (11) of the tubular element (9) are configured to allow a relative movement of the first and second containers (2, 3) between at least one position in which the tubular element (9) is spaced from the piercible barrier (17) and a position in which the tubular element (9) acts on the piercible barrier (17) so as to pierce it.

According to a 13th aspect in accordance with any one of the 5th to 12th aspects, the second container (3) comprises a base portion (12) defining a seat (15), the seat (15) being delimited at one end by the piercible barrier (17) and being delimited laterally by said wall (16) of the second container (3).

According to a 14th aspect in accordance with the 13th aspect, said wall (16) is at least partially shaped to match the mechanical connection means (11) of the tubular element (9) so as to engage in a fluid-tight manner around said tubular element (9).

According to a 15th aspect in accordance with the 13th or 14th aspect, the seat (15) has a substantially cylindrical or prismatic or truncated prism or frustoconical form.

According to a 16th aspect in accordance with any one of the 10th to 15th aspects, the mechanical connection means (11) of the tubular element (9) comprise peripheral projections configured to engage in a fluid-tight manner on said wall (16) of the second container (3).

According to a 17th aspect in accordance with any one of the 10th to 16th aspects, the mechanical connection means (11) of the tubular element (9) are of the type having at least one thread or of the snap-engaging or bayonet type.

According to a 18th aspect in accordance with any one of the 10th to 17th aspects, said wall (16) of the second container (3) is configured to be engaged in a fluid-tight manner with said connection means (11) of the tubular element (9).

According to a 19th aspect in accordance with any one of the 1st to 18th aspects, the first container (2) comprises a base portion (6) containing the first substance, said tubular element (9) being formed as one piece with the base portion (6).

According to a 20th aspect in accordance with the 19th aspect, the base portion (6) comprises a substantially flat support base (7) and an opposite wall (8) parallel to the support base (7), the tubular element (9) projecting transversely from said opposite wall (8).

According to a 21st aspect in accordance with the 19th or 20th aspect, the base portion (6) has a substantially cylindrical or prismatic or truncated prism or frustoconical form.

According to a 22nd aspect in accordance with any one of the 1st to 21st aspects, the first container (2) is formed as one piece.

According to a 23rd aspect in accordance with any one of the 1st to 22nd aspects, the second container (3) is formed as one piece.

According to a 24th aspect in accordance with any one of the 1st to 23rd aspects, the tubular element (9) has a first section with a substantially smooth outer surface configured to receive a spacer (4) and a second section comprising mechanical connection means (11) configured to engage the tubular element (9) with said wall (16) of the second container (3).

According to a 25th aspect in accordance with the 24th aspect:
  the tubular element (9) comprises mechanical connection means (11) configured to engage with said wall (16) of the second container (3),
  the second container (3) comprises a piercible barrier (17) and a base portion (12) defining a seat (15), the seat (15) being delimited at one end by the piercible barrier (17) and being laterally delimited by said wall (16) of the second container (3), said wall (16) being at least partially shaped to match the second section of the tubular element (9) so as to engage in a fluid-tight manner around said tubular element (9).

According to a 26th aspect in accordance with any one of the 1st to 25th aspects, the device (1) comprises a spacer (4) arranged between the first and second containers (2, 3).

According to a 27th aspect in accordance with the 26th aspect, the spacer (4) has substantially parallel oppositely arranged bases (20) intended to be arranged between and in contact with the first and second containers (2, 3).

According to a 28th aspect in accordance with the 26th or 27th aspect, the first container (2), the second container (3) and the spacer (4) have substantially the same radial size.

According to a 29th aspect in accordance with the 26th or 27th or 28th aspect, the spacer (4) has a substantially annular form comprising a gap (22) which allows the lateral extraction thereof even when the wall (16) of the second container (3) is engaged in a fluid-tight manner around the tubular element (9) of the first container (2).

According to a 30th aspect in accordance with any one of the 26th to 29th aspects, the spacer (4) comprises a lug (21) intended to allow easy movement thereof.

According to a 31st aspect in accordance with any one of the 1st to 30th aspects, the second container (3) comprises a base portion (12) and a collar (13) arranged on the opposite side to the base portion (12), the collar (13) being intended to be connected to a dispensing member (5), such as a dropper.

According to a 32nd aspect in accordance with the 31st aspect, the collar (13) has an opening (14) intended to allow, during use of the device (1), the passage of fluid.

According to a 33rd aspect in accordance with the 31st or 32nd aspect, the device (1) comprises a dispensing member (5), such as a dropper, configured to be engaged with the collar (13) of the second container (3).

According to a 34th aspect in accordance with the 33rd aspect, the dispensing member (5) is engaged with the collar (13) of the second container (3).

According to a 35th aspect in accordance with the 33rd or 34th aspect, the dispensing member (5) is configured to dispense drops while maintaining a sterile environment inside the second container (3).

According to a 36th aspect in accordance with the 33rd or 34th or 35th aspect, said dispensing member (5) and said collar (13) comprise mechanical connection means.

According to a 37th aspect in accordance with the 36th aspect, said mechanical connection means are of the type having at least one thread or of the snap-engaging or bayonet type.

According to a 38th aspect in accordance with any one of the 1st to 37th aspects, the first container (2) is made of a material having a hardness greater than the hardness of the material of the second container (3).

According to a 39th aspect in accordance with any of the 1st to 38th aspects, the first container (2) and the second container (3) comprise respective coatings, the coating of the first container (2) having a hardness greater than the hardness of the coating of the second container (3).

According to a 40th aspect a process for the production of a device (1) for dispensing eye drops is provided, the eye drop dispensing device (1) being preferably in accordance with any one of the 1st to 39th aspects, the process comprising at least the following steps:
  providing a first container (2), a second container (3) and a spacer (4),
  introducing a first substance inside the first container (2),
  introducing a second substance inside the second container (3), assembling the first container (2), the second container (3) and the spacer (4), said assembly step comprising arranging the spacer (4) between the first and second containers (2, 3).

freeze-drying the second substance.

According to a 41st aspect in accordance with the 40th aspect, the first substance is water or a water-based solution for injection.

According to a 42nd aspect in accordance with the 40th or 41st aspect, the second substance is a solution or dispersion comprising a drug. The drug may be of a chemical and/or biotechnological nature, for example may comprise the nerve growth factor.

According to a 43rd aspect in accordance with the 40th or 41st or 42nd aspect, the step of freeze-drying the second substance is performed following assembly and comprises subjecting the first container/second container/spacer assembly to a freeze-drying atmosphere.

According to a 44th aspect in accordance with the 43rd aspect, the first container (2) comprises a tubular element (9) with an open end portion (10), the second container (3) comprises a wall (16) configured to be engaged in a fluid-tight manner around the tubular element (9), a collar (13) with an opening (14) and a base portion (12) defining a seat (15), the seat (15) being delimited at one end by a piercible barrier (17) and being delimited laterally by said wall (16) of the second container (3).

According to a 45th aspect in accordance with the 44th aspect, the assembly step comprises engaging the tubular element (9) in a fluid-tight manner inside the seat (15).

According to a 46th aspect in accordance with the 45th aspect, the step of subjecting the first container/second container/spacer assembly to a freeze-drying atmosphere is performed so as to cause the outflow of an aqueous content of the solution or dispersion comprising the drug from the opening (14) of the collar (13), obtaining a freeze-dried composition (300) comprising the drug and so as to freeze the water or water-based solution for injection, the water or water-based solution for injection freezing without coming out of the seat (15) so that, following removal of the first container/second container/spacer assembly from the freeze-drying atmosphere, the water or water-based solution for injection becomes liquid again.

According to a 47th aspect in accordance with the 40th or 41st or 42nd aspect, the step of freeze-drying the second substance is performed before assembly and comprises subjecting the second container (3) to a freeze-drying atmosphere.

According to a 48th aspect in accordance with any one of the 40th to 47th aspects, the process comprises at least one step of sterilizing at least the first and the second containers (2, 3) and/or the spacer (4).

According to a 49th aspect in accordance with the 48th aspect, said at least one sterilization step is performed between the assembly step and the step for freeze-drying the second substance.

According to a 50th aspect in accordance with the 48th or 49th aspect, said at least one sterilization step is performed before introducing the first substance and the second substance inside the first and second containers (2, 3), respectively.

According to a 51st aspect in accordance with the 48th or 49th or 50th aspect, the sterilization is of the type using gamma rays or of the type using ethylene oxide or is performed with steam in an autoclave.

According to a 52nd aspect in accordance with any one of the 48th to 51st aspects, the process comprises providing a dispensing member (5) such as a dropper, said at least one sterilization step comprising sterilizing also the dispensing member (5).

According to a 53rd aspect in accordance with any one of the 40th to 52nd aspects, the process comprises providing a dispensing member (5) such as a dropper and engaging the dispensing member (5) with the second container (3).

According to a 54th aspect in accordance with the 53rd aspect, the step of engaging the dispensing member (5) with the second container (3) is performed in a sterile environment.

According to a 55th aspect in accordance with the 53rd or 54th aspect, the step of engaging the dispensing member (5) with the second container (3) is performed following freeze-drying of the second substance.

According to a 56th aspect in accordance with any one of the 40th to 55th aspects, the process comprises packaging the eye-drop dispensing device (1) inside a further sterile and/or hermetically sealed container.

According to a 57th aspect in accordance with the 56th aspect, the packaging step is performed following engagement of the dispensing member (5) with the second container (3).

According to a 58th aspect in accordance with the 56th or 57th aspect, the packaging step is performed in a nitrogen-containing atmosphere.

According to a 59th aspect in accordance with any one of the 40th to 58th aspects, the first container (2) comprises a tubular element (9) with an open end portion (10), the second container (3) comprises a wall (16) configured to be engaged in a fluid-tight manner around the tubular element (9), the assembly step comprising engaging in a fluid-tight manner the tubular element (9) with the wall (16).

According to a 60th aspect in accordance with any one of the 40th to 59th aspects, the first container (2) comprises a tubular element (9) with an open end portion (10) and the second container (3) comprises a piercible barrier (17) and a base portion (12) defining a seat (15) delimited at one end by the piercible barrier (17) and delimited laterally by a wall (16) of the second container (3), the assembly step comprising engaging the tubular element (9) inside the fluid-tight seat (15) on said wall (16) of the second container (3).

According to a 61st aspect in accordance with the 60th aspect, the assembly step comprises engaging the tubular element (9) inside the seat (15) so that the open end portion (10) of the tubular element (9) is positioned facing the piercible barrier (17).

According to a 62nd aspect in accordance with any one of the 40th to 61st aspects, the assembly step comprises: engaging the spacer (4) with the first container (2) and engaging the second container (3) with the first container/spacer assembly.

According to 63rd aspect in accordance with the 62nd aspect, the first container (2) comprises a base portion (6) comprising a substantially flat support base (7) and an opposite wall (8) parallel to the support base (7) and a tubular element (9) projecting transversely from said opposite wall (8), the step of engaging the spacer (4) with the first container (2) comprising positioning the spacer (4) around the tubular element (9) and close to or in contact with said opposite wall (8).

According to a 64th aspect in accordance with the 62nd or 63rd aspect, the second container (3) comprises a piercible barrier (17) and a base portion (12) defining a seat (15) delimited at one end by the piercible barrier (17) and delimited laterally by a wall (16) of the second container (3), the step of engaging the second container (3) with the first container/spacer assembly comprising positioning the tubular element (9) inside the fluid-tight seat (15) on said wall (16) of the second container (3).

According to a 65th aspect in accordance with the 62nd or 63rd or 64th aspect, the tubular element (9) comprises means (11) for mechanically connecting together the first and second containers (2, 3), the step of engaging the second container (3) with the first container/spacer assembly comprising engaging the second container (3) with the first container (2) by means of said connection means (11).

According to a 66th aspect in accordance with the 64th or 65th aspect, the second container (3) comprises a collar (13) arranged on the opposite side to the base portion (12), the process comprising providing a dispensing member (5), such as a dropper, and engaging the dispensing member (5) with the collar (13) of the second container (3).

According to a 67th aspect in accordance with any one of the 40th to 66th aspects, the step of providing the first container (2), the second container (3) and the spacer (4) comprises moulding the first container (2), the second container (3) and the spacer (4).

According to a 68th aspect a process for preparing a multidose eye-drop solution is provided, said process comprising the steps of:
 providing a first container (2), a second container (3) and a spacer (4), the first container (2) comprising a tubular element (9) with an open end portion (10) and the second container (3) comprising a piercible barrier (17) designed to separate substances intended to be contained inside the first container (2) and the second container (3),
 introducing water or water-based solution for injection (200) inside the first container (2),
 introducing a solution or dispersion comprising a drug inside the second container (3),
 assembling the first container (2), the second container (3) and the spacer (4), said assembly step comprising arranging the spacer (4) between the first and second containers (2, 3),
 freeze-drying the solution or dispersion comprising the drug so as to obtain a freeze-dried composition (300) comprising the drug,
 removing the spacer (4),
 piercing the barrier (17) by means of the said tubular element (9),
 mixing together water or water-based solution for injection (200) and freeze-dried composition (300) comprising the drug so as to obtain an eye solution.

According to a 69th aspect in accordance with the 68th aspect, the step of mixing water and water-based solution for injection (200) and freeze-dried composition (300) comprising the drug comprises the passage of water or water-based solution for injection (200) from the first container (2) into the second container (3).

According to a 70th aspect in accordance with the 68th or 69th aspect, the step of piercing the barrier (17) by means of said tubular element (9) is performed by moving the first container relative to the second container (3), or vice versa.

According to a 71st aspect in accordance with the 68th or 69th or 70th aspect, the second container (3) comprises a wall (16) configured to be engaged with the tubular element (9), the assembly step comprising engaging in a fluid-tight manner the tubular element (9) with the wall (16) of the second container (3).

According to a 72nd aspect in accordance with any one of the 68th to 71st aspects, the assembly step comprises positioning the tubular element (9) in the vicinity of the piercible barrier (17).

According to a 73rd aspect a process for preparing a multidose eye solution is provided, said process comprising the steps of:
 providing a device (1) for dispensing drops, the drop dispensing device (1) being preferably in accordance with any one of the 1st to 39th aspects and comprising:
  a first container (2) containing water or a water-based solution for injection (200), the first container (2) comprising a tubular element (9) with an open end portion (10),
  a second container (3) containing a freeze-dried composition (300) comprising a drug, the second container (3) comprising a collar (13) with an opening (14) and a piercible barrier (17) designed to separate water or water-based solution for injection (200) from the freeze-dried composition (300) comprising the drug,
  a dispensing member (5), such as a dropper, engaged with a collar (13) of the second container (3),
  a spacer (4) arranged between the first and second containers (2, 3),
 removing the spacer (4),
 piercing the barrier (17) by means of said tubular element (9),
 mixing together water or water-based solution for injection (200) and freeze-dried composition (300) comprising the drug so as to obtain an eye solution.

The drug may be of a chemical and/or biotechnological nature, for example may comprise the nerve growth factor.

According to a 74th aspect in accordance with the 73rd aspect, the process comprises dispensing one or more doses of eye solution by means of said dispensing member (5).

According to a 75th aspect in accordance with the 73rd or 74th aspect, the step of mixing water or water-based solution for injection (200) and freeze-dried composition (300) comprising the drug comprises the passage of water or water-based solution for injection (200) from the first container (2) into the second container (3).

According to a 76th aspect in accordance with the 73rd or 74th or 75th aspect, the step of piercing the barrier (17) by means of said tubular element (9) is performed by moving the first container relative to the second container (3), or vice versa.

BRIEF DESCRIPTIONS OF DRAWINGS

By way of a non-limiting example, the detailed description of one or more preferred embodiments of the invention is now provided, wherein:

FIG. 3 shows a cross-sectional view of the drop dispensing device in accordance with an embodiment of the present invention, in the assembled condition;

FIGS. 4 and 5 show cross-sectional views of a drop dispensing device in accordance with an embodiment of the present invention, in different assembled conditions.

DETAILED DESCRIPTION OF EMBODIMENTS OF THE INVENTION

Figure 2:
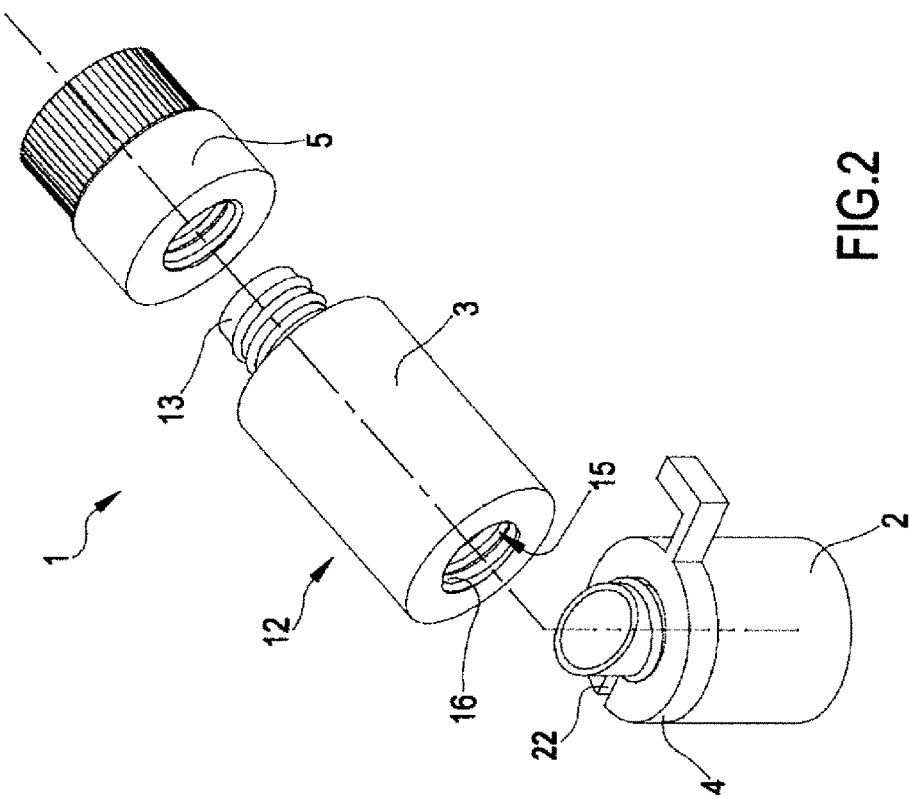
FIG. 2 shows a partial exploded view of the drop dispensing device of FIG. 1.

With reference to the figures, 1 denotes overall a device for dispensing drops. The drop dispensing device 1 comprises a first container 2, a second container 3, a spacer 4 and a dispensing member 5. Preferably the first container 2 is formed as one piece. The first container 2 comprises a base portion 6 containing water for injection (WFI) 200 or a water-based solution for injection. The base portion 6 has a support base 7 and an opposite wall 8, from which a tubular element 9 extends transversely. The tubular element 9 is formed as one piece with the base portion 6 and has an open end portion 10. The tubular element 9 also has mechanical connection means 11 designed to allow engagement of the first and second containers 2, 3. By way of example, the tubular element 9 may have a first, substantially smooth section intended to receive a spacer 4, and the mechanical connection means 11 may be defined along a second section of the tubular element 9. The mechanical connection means 11 may comprise at least one thread; alternatively, the connection means 11 may be of the snap-engaging or bayonet type. By way of example, the attached figures show a tubular element 9 provided with threaded connection means defined by peripheral projections extending along an outer surface of the tubular element 9. The open end portion 10 is intended to allow, in certain operating conditions of the drop dispensing device 1, the passage of water for injection 200 through it and therefore out of the first container 2.

The second container 3 contains a freeze-dried composition 300 comprising a drug, for example a nerve growth factor (NGF), and is configured to be engaged with the first container 2. Preferably, the second container 3 is formed as one piece. The second container 3 has a base portion 12 and a collar 13 provided with an opening 14 and defined on the opposite side to the base portion 12. A seat 15 delimited laterally by a wall 16 and at one end by a piercible barrier 17 extending transversely with respect to the wall 16 is defined on the base portion 12 of the second container 3. The seat 15 may have a substantially cylindrical form; alternatively, the seat 15 may have a substantially prism-like or truncated prism or frustoconical form. As shown in FIG. 3, in the assembled condition of the drop dispensing device 1, the tubular element 9 is housed at least partially inside the seat 15. The wall 16 is intended to be engaged in a fluid-tight manner with the mechanical connection means 11 of the tubular element 9; for this purpose, the wall 16 may be shaped to match the connection means 11 of the tubular element 9 or may have in turn connection means. The attached figures show a second container 3, the wall 16 of which is shaped to match the thread of the tubular element 9. In accordance with this embodiment, the first and second containers 2, 3 may be engaged or disengaged simply by screwing or unscrewing the second container 3 together with/from the first container 2. In order to ensure a fluid-tight connection between the first and second containers 2, 3, the first container 2 may be made of a material having a hardness greater than that of the material from which the second container 3 is made; for example, the first container 2 may be made of Teflon and the second container 3 may be made of polyethylene. By providing a harder material, or a coating, for the first container 2, the second container 3 may be deformed when the two containers are engaged together. In this way, when the tubular element 9 is inserted inside the seat 15 of the second container 3, the seat 15 itself is deformed so as to form a fluid-tight casing around the tubular element 9. As mentioned above, a collar 13 is defined on the opposite side to the base portion 12 of the second container 3 defining the seat 15, the dispensing member 5 being engaged with said collar in the assembled condition of the drop dispensing device 1 (see FIG. 3). The dispensing member 5 comprises a fluid dispensing opening 18 in fluid communication with the second container 3. As shown in the attached figures, the dispensing member 5 may consist for example of a dropper. The collar 13 and the dispensing member 5 may have mechanical connection means 19; the attached figures show, for example, a collar 13 provided with threaded connection means 19 and a dispensing member 5 internally shaped to match the threading of the collar 13 (see FIGS. 3 to 5). Alternatively, the connection means 19 may be of the snap-engaging or bayonet type.

The dispensing member 5 is configured to allow dispensing of a multidose eye solution prepared from water for injection 200 and freeze-dried composition 300 comprising the drug, as will be described in greater detail below. In particular, the dispensing member 5 (shown only schematically in FIGS. 3 to 5) is configured to dispense drops of eye solution while maintaining a sterile environment inside the second container 3. Owing to this particular characteristic of the dispensing member 5 it is possible to design the dispensing device 1 so that the eye solution prepared with it may be multidose. In other words, from the moment the solution is prepared inside the dispensing device 1, the solution may be used for a prolonged period, up to 90 days after opening, and this usually allows a therapy cycle to be completed using a single dispensing device 1. A dispensing member 5 able to preserve the sterility of the container is for example commercially distributed under the trade name Novelia®, by Nemera La Verpillière, France.

Figure 1:
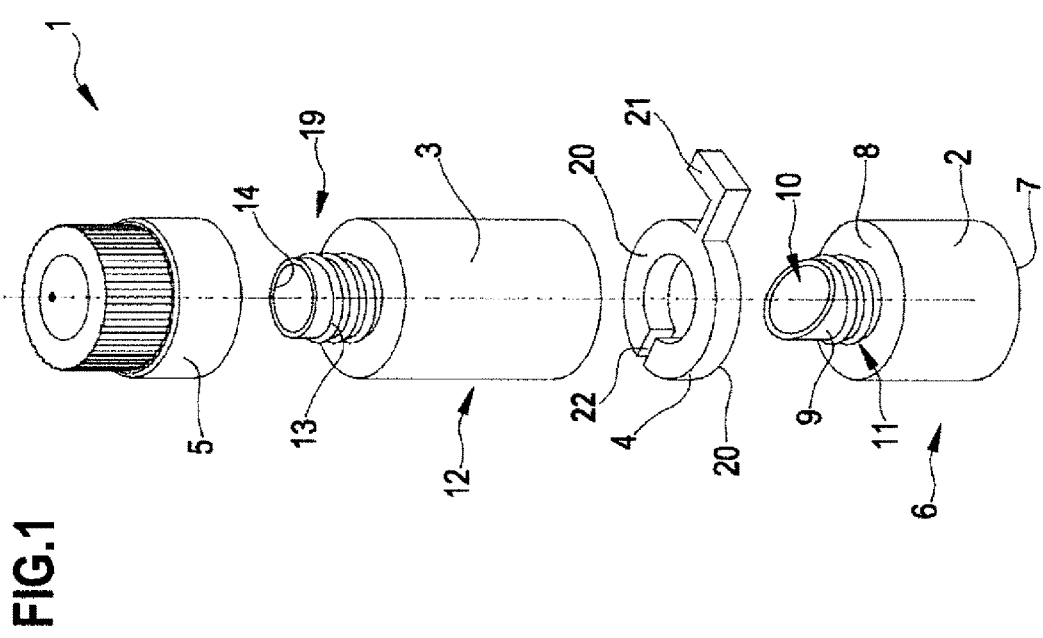
FIG. 1 shows an exploded view of the drop dispensing device in accordance with an embodiment of the present invention.

The spacer 4 has moreover opposite and parallel bases 20 which, in the configuration where the spacer 4 is engaged with the first and second containers 2, 3, make contact with the first and second containers 2, 3 (see FIG. 3). Therefore, in the assembled condition of the drop dispensing device 1, the spacer 4 is engaged between the first and second containers 2, 3. The contact between the bases 20 of the spacer 4 and, respectively, the first and second containers 2, 3 prevents the latter from being able to be inadvertently moved closer together. By way of example, the spacer 4 may consist of an O-ring or resilient ring. The spacer 4 has a substantially annular form and comprises a gap 22 which allows the lateral extraction of the spacer even when the wall 16 of the second container 3 is engaged in a fluid-tight manner around the tubular element 9 of the first container 2. In this way the spacer 4 may be removed without disassembling the device 1, safeguarding therefore the sterility of the device itself 1 and its contents. Preferably the spacer 4 has a main body having substantially the same radial size compared to the first and second containers 2, 3. Providing the first container 2, second container 3 and spacer 4 with the same radial size is particularly advantageous since it increases the compactness of the eye-drop dispensing device 1. Optionally, the spacer 4 comprises a lug 21 designed to allow easy movement thereof (see FIGS. 1-3). As shown in FIG. 3, the spacer 4 is able to prevent, in the assembled condition of the drop dispensing device 1, the tubular element 9 from coming into contact with the piercible barrier 17. The piercible barrier 17 operates between a closed condition (barrier not perforated, see FIG. 3), in which it prevents mixing of water for injection and freeze-dried composition 300 comprising the drug, and an open condition (barrier pierced or open, see FIG. 5), in which it allows mixing of water for injection 200 and freeze-dried composition 300 comprising the drug. In the assembled condition of the drop dispensing device shown in FIG. 3, the piercible barrier 17 is in a closed condition in which it delimits at the top the seat 15 defined by the second container 3 and prevents mixing together of the substances contained respectively inside the first and second containers 2, 3. Following removal of the spacer 4 and a movement of the first container 2 against the second container 3 (or vice versa), the tubular element 9 comes into contact with the piercible barrier 17, piercing it or causing opening thereof (see FIG. 5). FIG. 4 instead show a configuration of the drop dispensing device 1 in between the configuration shown in FIG. 3 and that shown in FIG. 5, where the spacer 4 has been removed from the drop dispensing device 1, but the tubular element 9 does not act on the piercible barrier 17. After piercing the barrier 17, the two substances contained inside the first and second containers 2, 3 may be mixed together by simply shaking the drop dispensing device 1. Mixing together of the two substances allows the preparation of a multidose eye solution. The multidose eye solution may therefore be dosed and dispensed by means of the dispensing member 5.

The present invention relates moreover to a process for the production of a device 1 for dispensing eye drops, in accordance with Claim 1.

In accordance with a first embodiment of the process, water for injection 200 or a water-based solution for injection is introduced inside the first container 2. Then, the spacer 4 is engaged with the first container 2 around the tubular element 9; in this connection, see the first container/spacer assembly shown in FIG. 2. At this point, the second container 3 is engaged with the first container/spacer assembly; this engagement ensures a fluid-tight seal between the first container 2 and the second container 3 and prevents therefore the substance contained inside the first container 2 from coming out of the seat 15 inside which tubular element 9 is engaged in a fluid-tight manner. In particular, the fluid is prevented from coming out of the first container 2 by the provision of the piercible barrier 17 which closes the seat 15 at the top and by the fluid-tight engagement between tubular element 9 and wall 16 laterally delimiting the seat 15.

Following engagement of the second container 3 with the first container/spacer assembly, sterilization of the first container/second container/spacer assembly is performed. Sterilization may be of the type using gamma rays or ethylene oxide or may be of the type performed using steam in an autoclave. Thereafter a solution or dispersion comprising a drug is introduced inside the second container 3. The drug may be of a chemical and/or biotechnological nature, for example may comprise the nerve growth factor. At this point of the process, the first container 2 contains water for injection 200 and is engaged in a fluid-tight manner with the second container 3, and the second container 3 contains the solution or dispersion comprising the drug; the second container 3 is open in the region of the collar 13.

The first container/second container/spacer assembly is then subjected to a freeze-drying atmosphere; for this purpose it may be inserted inside a freeze-drying chamber. The freeze-drying atmosphere may for example have a temperature of between −90° C. and −20° C., preferably between −50° C. and −30° C. for primary drying and a temperature of between −15° C. and +35° C., preferably of between −5° C. and +15° C. for secondary drying; the vacuum pressure during the process may have a value of between 20 and 300 μbar (microbar). The freeze-drying atmosphere allows freeze-drying of the solution or dispersion comprising the drug and allows therefore a freeze-dried composition 300 comprising the drug to be obtained. The freeze-drying operation removes the water content of the solution or dispersion comprising the drug; this water content flows out from the second container 3 through the opening 14 of the collar 13. Since the first container 2 is engaged in a fluid-tight manner with the second container 3, the freeze-drying atmosphere instead does not allow freeze-drying of the water for injection 200 contained in the first container 2; the water for injection 200 freezes inside the first container 2, without however being able to flow out of it or the seat 15 inside which the tubular element 9 is engaged. Since it is confined inside the first container, the water for injection 200 returns to the liquid state following removal of the freeze-drying atmosphere.

At this point, a dispensing member 5 is engaged with the collar 13 of the second container 3 so as to obtain a device 1 for dispensing eye drops, the dispensing member 5 may be engaged with the collar 13 by simply screwing it together therewith. Engagement of the dispensing member 5 may be performed in a sterile environment. The device 1 for dispensing eye drops thus obtained is shown in FIG. 3.

The process then involves a step for packaging the eye-drop dispensing device 1; the packaging step is preferably performed in a nitrogen-containing atmosphere. The packaging step may involve placing the eye-drop dispensing device 1 inside a further sterile or hermetically sealed container.

In accordance with a second embodiment of the process, the first container 2 and the second container 3 are sterilized first of all. This step may also involve the sterilization of the dispensing member 5 and the spacer 4. The sterilization may be of the type using gamma rays or ethylene oxide or may be of the type using steam performed in an autoclave. In accordance with the second embodiment of the process, one or more of the steps following sterilization, which will be described below, may be performed in a sterile environment. Following sterilization, water for injection 200 is introduced inside the first container 2. A spacer 4 is then engaged with the first container 2 around the tubular element 9. A solution or dispersion comprising the drug is introduced inside the second container 3; during this step, the second container 3 is not assembled with the first container 2. The second container 3 is then subjected to a freeze-drying atmosphere which has the same temperature and pressure values described above; in this way freeze-drying of the solution or dispersion comprising the drug contained inside the second container 3 occurs. In accordance with the second embodiment, the first container 2 is not subjected to the freeze-drying atmosphere. At the end of the freeze-drying process, the second container 3 therefore contains a freeze-dried composition 300 comprising the drug. Following freeze-drying, the dispensing member 5 is engaged with the collar 13 of the second container 3; the engagement of the dispensing member 5 may be performed in a sterile environment. In order to perform assembly of the drop dispensing device 1, the second container/dispensing member assembly is engaged with the first container/spacer assembly. This assembly operation may be performed so that the first container 2 is connected in a fluid-tight manner with the second container 3 (as described above) in order to prevent leakage of fluid between said containers. The device 1 for dispensing eye drops thus obtained is shown in FIG. 3.

The process then envisages a step for packaging the eye-drop dispensing device 1; the packaging step is preferably performed in a nitrogen-containing atmosphere. The packaging step may involve placing the eye-drop dispensing device 1 inside a further sterile or hermetically sealed container.

The use of the eye-drop dispensing device 1 will be described below. The use of the eye-drop dispensing device 1 involves substantially the preparation of a multidose eye solution.

To allow preparation of the eye solution, from the assembled condition of the eye-drop dispensing device 1, the spacer 4 is removed laterally from the eye-drop dispensing device 1. Owing to the presence of the gap 22, the spacer 4 may be removed without disengaging the first container 2 from the second container/dispensing member assembly. At this point, the first container 2 and the second container 3 are moved relatively closer together; for example, this operation may be performed by means of rotational movement of the second container 3 with respect to the first container 2 (as shown in FIG. 5) or vice versa. The movement of the first and second containers 2, 3 is made possible owing to the provision of the connection means described above. This movement allows the barrier 17 of the second container 3 to be pierced by means of the tubular element 9 of the first container 2 (see FIG. 5). After piercing the barrier 17, in order to obtain the eye solution, mixing of water for injection 200 and freeze-dried composition 300 comprising the drug, for example nerve growth factor, is performed.

As mentioned above, the freeze-dried composition 300 comprising the drug is introduced inside the second container 3, with which the dispensing member 5 is engaged. During use of the drop dispensing device 1, owing to the provision of the freeze-dried composition 300 in the proximity of the dispensing member 5, by shaking the drop dispensing device 1, water for injection may be made to flow out of the first container 2 into the second container 3 and consequently mixing is performed mainly inside the second container 3, thus avoiding having the freeze-dried composition 300 comprising the drug inside the first container 2.

Following mixing, during use of the drop dispensing device 1, dosing and subsequent application of the eye drops is performed by dosing them by means of the dispensing member 5. The application of the eye drops thus prepared may be repeated for several days, up to a maximum of 90 days.

As a result of the present invention it is possible to obtain one or more of the following advantages and solve one or more of the problems encountered in the prior art. Firstly, with the invention it is possible to obtain an eye-drop dispensing device which is compact, simple and ergonomic.

The invention also provides a process for the production of a drop dispensing device which may be automated in a simple and reliable manner.

The invention also provides a process for the preparation of an eye solution which is simple and may be rapidly implemented.

The invention is also convenient to use, easy to implement and simple and low-cost to produce.

The invention claimed is:

1. Process for production of a device for dispensing eye drops, comprising steps of:
   providing a first container comprising a tubular element with an open end portion;
   providing a second container comprising a wall engageable in a fluid-tight manner around the tubular element;
   providing a spacer having oppositely arranged bases which are substantially parallel;
   introducing water or a water-based solution for injection inside the first container;
   introducing a solution or a dispersion comprising a drug of one or more of a chemical and biotechnological nature inside the second container;
   arranging the spacer between the first and second containers so that the bases are in contact with the first and second containers;
   engaging in a fluid-tight manner the wall of the second container around the tubular element of the first container; and
   freeze-drying the solution or the dispersion comprising the drug;
   wherein the step of freeze-drying the solution or the dispersion comprising the drug is performed following assembly of the first and second containers with the spacer and comprises subjecting the assembly of the first container and the second container and the spacer to a freeze-drying atmosphere.

2. The process according to claim 1, further comprising steps of providing a dispensing member and engaging the dispensing member with the second container.

3. The process according to claim 2, wherein the dispensing member is a dropper.

4. The process according to claim 2, wherein the step of engaging the dispensing member with the second container is performed in a sterile environment and is performed following the step of freeze-drying the solution or the dispersion comprising the drug.

5. The process according to claim 4, further comprising a step of packaging the eye-drop dispensing device in one or more of a sterile and hermetically sealed container, the packaging step being performed following the step of engaging the dispensing member with the second container and being performed in a nitrogen-containing atmosphere.

6. The process according to claim 1, wherein the drug of the one or more chemical and biotechnological nature comprises a nerve growth factor (NGF).

7. The process according to claim 1, wherein the second container comprises a collar with an opening and a base portion defining a seat, the seat being delimited at one end by a piercible barrier and being delimited laterally by said wall of the second container, the assembly step comprising engaging the tubular element of the first container in a fluid-tight manner inside the seat, the step of subjecting the assembly to the freeze-drying atmosphere being performed so as to cause a water content of the solution or the dispersion comprising the drug to flow out from the opening of the collar obtaining a freeze-dried composition comprising the drug and so as to freeze the water or the water-based solution for injection, the water or the water-based solution for injection freezing without coming out of the seat so that, following removal of the assembly from the freeze-drying atmosphere, the water or the water-based solution for injection becomes liquid again.

8. The process according to claim 7, wherein the second container comprises a piercible barrier designed to separate substances intended to be contained inside the first container and the second container, the process comprising further a multidose eye drop solution preparing step comprising the steps of:
   removing the spacer;
   piercing the barrier using said tubular element;
   mixing together the water or the water-based solution for injection and the freeze-dried composition comprising the drug following the freeze-drying step so as to obtain an eye solution.

9. The process according to claim 1, comprising at least one step for sterilization of one or more of at least one of the first and second containers, the spacer, and the dispensing member, the sterilization being of a type using gamma rays or of a type using ethylene oxide or of a type performed using steam in an autoclave.

10. The process according to claim 9, wherein said at least one sterilization step is performed between assembly of the first and second containers with the spacer and the step for freeze-drying the solution or the dispersion comprising the drug.

11. The process according to claim 9, wherein said at least one sterilization step is performed before introducing the water or the water-based solution for injection and introducing the solution or the dispersion comprising the drug, respectively inside the first and second containers.

12. The process according to claim 1, wherein the second container comprises a piercible barrier and a base portion defining a seat delimited at one end by the piercible barrier and delimited laterally by the wall of the second container and being fluid tight, assembly of the first and second containers with the spacer further comprising step of engaging the tubular element of the first container inside the fluid-tight seat on said wall of the second container so that the open end portion of the tubular element is positioned facing the piercible barrier.

13. The process according to claim 1, wherein assembly of the first and second containers with the spacer further comprises steps of:
engaging the spacer with the first container; and
engaging the second container with assembly of the first container and the spacer;
the first container comprising a base portion comprising a substantially flat support base and an opposite wall parallel to the support base and the tubular element projecting transversely from said opposite wall, the step of engaging the spacer with the first container comprising positioning the spacer around the tubular element and close to or in contact with said opposite wall; and
the second container comprising a piercible barrier and a base portion defining a seat delimited at one end by the piercible barrier and delimited laterally by the wall of the second container, the step of engaging the second container with the assembly of the first container and the spacer comprising positioning the tubular element inside the seat in a fluid-tight manner on said wall of the second container.

14. The process according to claim 13, wherein the tubular element comprises means for mechanically connecting together the first container and the second container, and wherein the step of engaging the second container with the assembly of the first container and the spacer comprising engaging the second container with the first container using said means for mechanically connecting.

* * * * *